(12) United States Patent
Rahman

(10) Patent No.: US 7,554,493 B1
(45) Date of Patent: Jun. 30, 2009

(54) FOLDED MONOPOLE ANTENNA FOR IMPLANTED MEDICAL DEVICE

(75) Inventor: M. Mizanur Rahman, Stevenson Ranch, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1054 days.

(21) Appl. No.: 10/615,081

(22) Filed: Jul. 8, 2003

Related U.S. Application Data

(60) Provisional application No. 60/394,891, filed on Jul. 8, 2002.

(51) Int. Cl.
*H01Q 1/24* (2006.01)
(52) U.S. Cl. ............... 343/702; 343/872; 607/60
(58) Field of Classification Search .......... 343/702, 343/806, 829, 846, 872, 873; 607/4, 5, 9, 607/30–32, 59, 60; 128/920
See application file for complete search history.

(56) References Cited

U.S. PATENT DOCUMENTS

| | | | |
|---|---|---|---|
| 4,681,111 A | 7/1987 | Silvian | |
| 5,058,581 A | 10/1991 | Silvian | |
| 5,562,713 A | 10/1996 | Silvian | |
| 5,861,019 A | 1/1999 | Sun et al. | |
| 5,912,648 A | 6/1999 | Walthers | |
| 6,008,762 A | 12/1999 | Nghiem | |
| 6,054,955 A | 4/2000 | Schlegel, Jr. et al. | |
| 6,133,890 A | 10/2000 | Damiani | |
| 6,147,652 A * | 11/2000 | Sekine | 343/702 |
| 6,218,992 B1 | 4/2001 | Sadler et al. | |
| 6,240,317 B1 * | 5/2001 | Villaseca et al. | 607/60 |
| 6,259,418 B1 | 7/2001 | Jones et al. | |
| 6,285,336 B1 | 9/2001 | Zimmerman | |
| 6,317,099 B1 | 11/2001 | Zimmerman et al. | |
| 6,342,857 B1 | 1/2002 | Lane | |
| 6,379,300 B1 | 4/2002 | Haubrich | |
| 6,456,256 B1 * | 9/2002 | Amundson et al. | 343/873 |

FOREIGN PATENT DOCUMENTS

EP        1166820 A2        1/2002

* cited by examiner

*Primary Examiner*—Michael C Wimer
(74) *Attorney, Agent, or Firm*—Wong, Cabello, Lutsch, Rutherford & Brucculeri, LLP

(57) ABSTRACT

A folded monopole RF telemetry antenna is contained within a dielectric portion of an implantable medical device housing, which dielectric portion can be a biocompatible epoxy. The monopole antenna is formed from a wire or strip of conductive material which may be conformed inside the outer boundary of the epoxy housing. One end of the monopole antenna is free inside the epoxy, the other end of the antenna is electrically coupled to the circuit ground which, in turn, is connected to the metal housing portion, acting as a ground plane. The length of the antenna can be sized to be self-resonating at a frequency of about 403.5 MHz with at least a 3 MHz bandwidth.

28 Claims, 4 Drawing Sheets

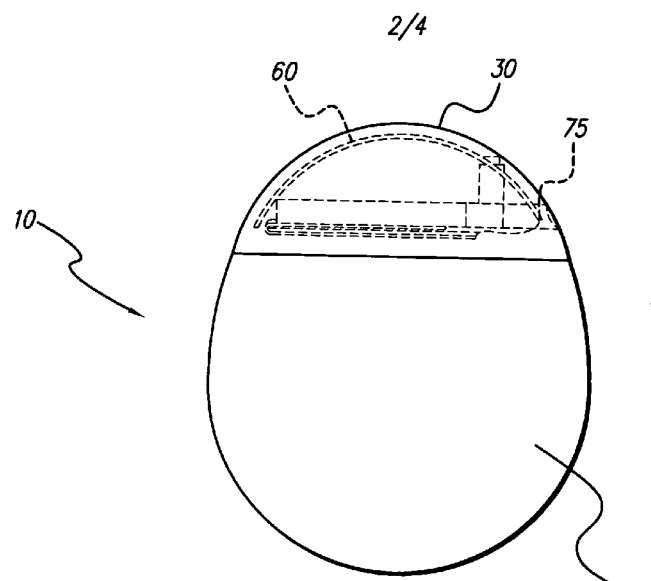
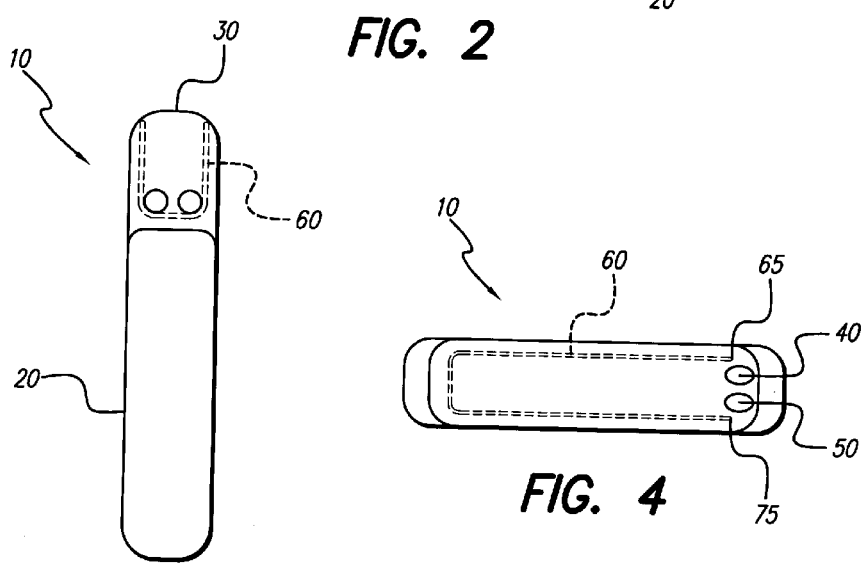

FOLDED MONOPOLE ANTENNA FOR IMPLANTED MEDICAL DEVICE

The present application claims the benefit of U.S. Provisional Application Ser. No. 60/394,891, filed 8 Jul. 2002, which application is herein incorporated by reference in its entirety.

BACKGROUND OF THE INVENTION

The present invention relates to implantable medical devices and, more particularly, to RF telemetry antennas used in such devices.

As technology has advanced in the development of implantable medical devices, communication with such devices has become increasingly more important. Communication is necessary to program a device, to monitor its various functions and to provide data concerning a patient's response to the device's therapy.

Radio frequency transmissions (RF) are commonly employed to communicate with an implantable medical device. A conventional RF telemetry transmission system generates low amplitude magnetic fields by oscillating current in an LC circuit. An RF telemetry antenna can transmit these signals and a receiving RF telemetry antenna can capture these same signals as induced currents within the receiving antenna.

Typically, an implantable medical device has an antenna which can receive and transmit RF transmission signals. Likewise, a separate external device incorporates an antenna which can receive and transmit RF transmission signals from and to the medical device. The external device may be a "programmer" which can transmit (down-link) and receive (up-link) analog and digital data to and from an implantable medical device. As such, the term "programmer" will be used hereinafter to refer to any external device which can provide and control down-link and/or up-link telemetry transmissions with the implantable medical device. The up-linked data is provided from a register or memory within the implantable device. Similarly, down-linked data can be stored in a register or memory in the implantable device.

Analog data which can be up-linked include values for battery voltage, sampled intracardiac electrocardiogram amplitudes, sensor output signals, pacing pulse amplitudes, energy consumption, pulse-width and pacing lead impedance. Digital data which can be transmitted include statistics related to performance, event markers, current values of programmable parameters, implant data, and patient and device identifier codes. These analog and digital data may be telemetered from many kinds of implantable medical devices, including implantable cardiac pacemakers, cardioverter-defibrillators, drug infusion pumps, cardiac and other physiologic monitors, nerve and muscle stimulators, deep brain stimulators, cochlear implants and artificial hearts.

As implantable medical devices have become more complex and capable of greater data processing, greater performance demands have been placed on the device's telemetry transmission system. It is desirable to have a telemetry system that permits large quantities of data to be transmitted in the shortest time interval, while maintaining high transfer reliability. Greater processing capability also, unfortunately, generally translates to higher usage of available power. Thus, there are competing factors which must be considered in designing an RF telemetry system. Such a telemetry system should ideally provide reliable and rapid transmission, yet conserve the device's battery power.

An important component of the RF telemetry system is the transmitting antenna. Use of RF antennas are common in the non-medical arts as provided in the following U.S. Pat. Nos. 5,912,648; 6,008,762; 6,054,955; 6,133,890; 6,218,992 B1; 6,259,418 B1; 6,285,336 B1; 6,317,099 B1; and 6,342,857 B1. Use of an RF telemetry antenna in an implantable medical device presents unique challenges because such a device is implanted in body tissue and the antenna must fit on or inside the compact housing of the medical device.

In addition, there are imposed regulatory limitations on permissible transmission frequencies and radiating power. Medical devices have been allocated a set frequency band in the UHF spectrum, specifically from 402 to 405 MHz, by the United States FCC (Federal Communications Commission), by the CEPT (Conference Européenne des Administration des Postes et des Telecommunications, i.e., the European Conference of Postal and Telecommunications Administrations) and by MICS (Medical Implant Communications Service). These agencies have also set a standard for maximum allowable Equivalent Isotropically Radiated Power (EIRP) emanating from an implantable medical device at a very low 25 µW. It is necessary, therefore, to have an efficient antenna for receiving this weak signal. At the same time, the antenna should have a relatively wide bandwidth of at least 3 MHz, so as to efficiently capture a telemetry signal anywhere within the allowable 402 to 405 MHz frequency band.

One factor affecting performance of the antenna is the housing of an implantable medical device, which housing is typically a conductive metal such as titanium. This metal housing affects the choice of antenna topology. The presence of a metal housing can adversely attenuate the radiated RF field and severely limit the operable distance for effective data transfer between the programmer and the implanted medical device to as short as a few inches.

Another factor that affects the performance of the antenna is the fact that the medical device is placed in surrounding body tissues which can change the RF characteristics of the antenna. Medical devices can be implanted in various parts of the body. For example, cardiac pacemakers can be implanted close to the clavicle and near the surface of the skin. Other devices, such as spinal cord stimulators, may be implanted in the abdomen under a thick layer of muscle, fascia and skin. These interposing body tissues can change the effective wavelength of the RF signals received by an antenna in the implanted device. Body tissues are conductive dielectric materials, i.e., they have relatively high dielectric constants ($\xi_r$) and exhibit conductivity ($\sigma$) which results in significant signal losses. For example, the conductivity of muscle tissue is between about 0.05 and 1.4 S/m. The dielectric constant can provide a measure of the reduction of the wavelength within a tissue. The dielectric constant of muscle tissue (in the UHF band) is between 50 and 80, while for comparison, the dielectric constant of air is about 1. Since the wavelength is reduced in body tissue, the electrical length of the antenna is effectively increased. The dielectric constants and conductivities of different tissues also vary with the frequency of the RF transmission signal. Increasing the frequency of the transmission signal increases the signal propagation loss. The losses owing to tissue conductivity are balanced to some extent by an efficiency gained from the wavelength reduction in the tissue.

If the antenna design (and the telemetry system) can only operate in a very narrow bandwidth, data transmission may not be reliable in clinical use. A broader bandwidth enables information to be transmitted more quickly and with greater reliability. In addition the assigned bandwidth between 402 and 405 MHz is divided into 10 channels in 300 KHz increments. Transmitting over many channels using one antenna provides greater flexibility for the telemetry system. To take full advantage of all channels available, it is desirable to have an antenna which is able to receive and send transmissions over the full frequency range of 402 to 405 MHz.

Still another factor which affects the antenna performance is the size of an implantable, medical device which the antenna must be attached to or placed in. Container size is problematic, for example, with a standard monopole antenna which is likely to be too large. A monopole antenna has a conductor material which has a free end and an end which is electrically connected. This antenna should have a length which is one-quarter of a wavelength (λ) long and, as is, this antenna is not practical for use in an implantable medical device. Specifically, a monopole that is shorter than λ/4 will not resonate at the desired frequency of around 403 MHZ and will require extra circuit components to tune the antenna to achieve the desired resonance frequency. The use of extra tuning components will result in loss of needed battery power.

A number of other antenna designs have been made or proposed to solve the design constraints of implantable antennas. A conventional example is a loop antenna which is used in commercially available medical devices. A loop antenna has two ends, each end having an electrical connection. While a loop antenna is advantageously compact and can be designed to work in a medical device, there are drawbacks inherent to this design. For example, the design suffers from a relatively low efficiency, a small operating range and a narrow bandwidth. As a result, extra power-consuming circuitry may be necessary to compensate for these deficiencies.

In one design, disclosed in U.S. Pat. No. 4,681,111 to Silvian, a stub antenna associated with the header is employed as the implantable antenna for high carrier frequencies of up to 200 MHz and employing phase shift keying (PSK) modulation. In another design, disclosed in U.S. Pat. Nos. 5,058,581 and 5,562,713 issued to Silvian, an RF telemetry antenna uses the elongated wire conductor of one or more medical leads extending away from the implanted medical device. In the examples provided, the medical lead is a cardiac lead used to deliver electrical stimulation energy to the heart from an implantable pulse generator (IPG) and to conduct electrical heart signals back to a sense amplifier within the IPG. The conductor wire of the medical lead can operate as a far field radiator to a more remotely located programmer RF telemetry antenna. Advantageously, it is not necessary to maintain a close spacing between the programmer RF telemetry antenna and the implanted cardiac lead antenna. Consequently, the antenna is less sensitive to patient movement during telemetry transmission.

There are, however, disadvantages with this lead design. Because the radiating field is maintained by the current flowing in the lead conductor, RF telemetry transmission via the lead conductor may conflict with sensing and stimulation operations. The elongated lead wire, which is the RF telemetry antenna, has directional radiation nulls dependent on the placement direction of the medical lead, which direction can vary with each patient. Both of these factors often necessitate that the up-link telemetry transmission energy be set very high to ensure that the RF transmission is detected at the programmer telemetry antenna. In addition, the design cannot be used in all implantable medical devices, such as drug infusion pumps and artificial hearts, because these do not have stimulating leads extending from the medical device.

A microstrip antenna design is disclosed in U.S. Pat. No. 5,861,019. The antenna is formed on or within the exterior surface of an implantable device housing. The microstrip patch is formed of an electrically conductive radiator patch that is laminated upon one side of a dielectric substrate layer.

Thus, it is apparent that there is a continuing need for a more efficient and compact antenna system that can be used with an implantable medical device having a metal housing.

It is further apparent that there is a need for such an antenna system which has high transmission reliability, conserves battery power, and can operate under other design and regulatory limitations imposed on a body implantable medical device.

SUMMARY OF THE INVENTION

The present invention addresses the above and other needs by overcoming the disadvantages enumerated above, and also allows an additional degree of freedom in scaling the level of the detected signal.

An improved RF telemetry antenna system is provided comprising a folded monopole antenna which is electrically coupled to a metal pad located on an internal circuit board. This metal pad is coupled to a transceiver circuit for receiving and transmitting signals. There is a circuit ground which is coupled to a second metal pad and which is further coupled to the metal housing portion. The metal housing portion acts as an antenna ground plane which effectively lengthens the antenna by lengthening the current path. The antenna can be constructed of a wire or thin conductive strip that is conformable inside a biocompatible, dielectric portion of the housing. The antenna can be designed to self-resonate at the desired frequency of about 403.5 MHz and may be tunable by sizing the length of the wire or conductive strip within a dielectric housing.

It is thus a feature of the present invention to provide a compact, self-resonating RF telemetry antenna system for use in an implantable medical device.

It is another feature of the present invention to provide the capability of tuning the resonant frequency of the antenna by physically pre-sizing the length of the monopole antenna and thereby avoid the use of an additional power-consuming, tuning circuitry.

It is further a feature of the present invention to provide an antenna system which uses the metal portion of the implanted device housing as a ground plane to effectively increase the antenna length.

It is yet another feature of the present invention to provide an antenna system with sufficient bandwidth to facilitate rapid transmission of large quantities of data.

BRIEF DESCRIPTION OF THE DRAWINGS

The above and other aspects, features and advantages of the present invention will be more apparent from the following particular description thereof, presented in conjunction with the following drawings wherein:

FIG. 2 is a front view of the stimulation device of FIG. 1, showing the antenna system of the present invention;

FIG. 3 is a left side view of the stimulation device of FIG. 1, showing a left side view of the antenna system of the present invention;

FIG. 4 is a top view of the stimulation device of FIG. 1, showing the top view of the antenna system of the present invention;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

A self-resonating, folded monopole antenna system for use in an implantable medical device is disclosed herein. The antenna is intended to be used with a programmer transceiver to down-link data to the medical device or up-link telemetered data from the medical device to the programmer. In this improved antenna design, the metal portion of the device housing is employed as a ground plane of the antenna. In addition, to provide added antenna length within the confines of the device housing, the monopole antenna is folded once to conform to the periphery of the epoxy portion of the housing. These features solve the unique challenges of having to enclose an antenna within a compact medical device and yet, at the same time, having to receive and send RF transmissions in the 402-405 MHz frequency range.

In accordance with the present invention, a preferred embodiment of the antenna will be discussed in the context of use within an implantable spinal cord stimulator that is used to treat intractable pain and is intended to be implanted in a patient's abdomen.

Figure 1:
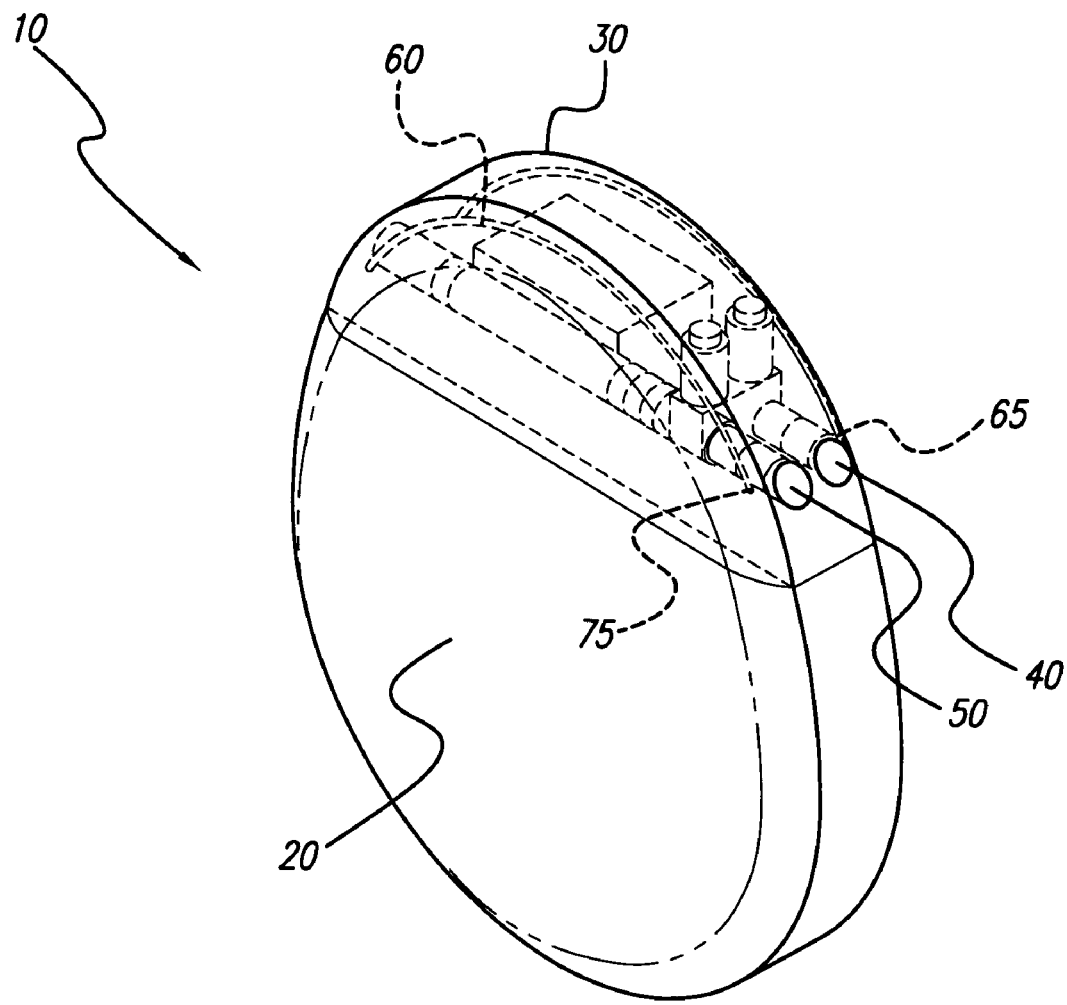
FIG. 1 is a perspective view of the implantable stimulation device showing the antenna system of the present invention.

FIG. 1 shows, in accordance with the present invention, a perspective view of an exemplary embodiment of an RF telemetry system which comprises a folded monopole antenna 60 within an implantable spinal cord stimulator 10. The housing may be comprised of two parts, a metal portion 20 and an epoxy portion 30. The metal housing portion 20 of the implanted device is approximately a partial elliptical cylinder, having the following dimensions: a 55 millimeter major axis, a 45 millimeter minor axis and a 9 millimeter thickness. The metal portion of the housing deviates from an elliptical cylinder in that a portion of the elliptical cylinder is replaced by an epoxy portion 30. The epoxy portion has openings 40 and 50 to permit stimulation leads (not shown) to be inserted through the epoxy and coupled to lead connections, which are electrically connected to stimulation circuits inside the stimulator. The stimulator is preferably flat and thin to facilitate implantation under fascia, muscle and skin. All exterior edges of the stimulator are rounded to eliminate sharp edges.

The antenna 60 is shown as a thin conductive wire which can be easily conformed into a desired shape. The antenna shown has a free end 65 and a connection end 75. The antenna can be shaped as two separate arcs that are in planes that are substantially parallel to each other. It will be appreciated that, in addition to the conductor in the form of a wire, the conductor may be any suitable conformable, elongate configuration including a thin conductor strip having a definable first end and second end. The wire antenna, as shown in FIG. 1, runs along the curved outer edge within the epoxy housing 30 to maximize the separation between the metal housing and the antenna. This separation helps reduce RF transmission reception distortion and interference from the metal housing. Because the free end 65 of the antenna is not electrically connected, the antenna is effectively a folded monopole having one electrical connection at connection end 75.

The stimulator 10 may contain a microprocessor and an electrical circuit designed to deliver stimulation pulses through the connected leads and may include sense amplifiers which can detect the lead and tissue impedance. The circuit may further include memory registers or RAMS for storing a variety of programmed operating modes and parameters to shape the stimulation pulse regime. Some of these parameters include pulse-width, frequency of stimulation, monopolar or bipolar electrode configuration, pulse amplitude envelopes, and uniphasic or biphasic stimulation. The device may also collect data pertaining to patient condition.

FIG. 2 shows, in accordance with the invention, a front view of the stimulator 10, and a folded monopole antenna 60, within the epoxy portion 30.

FIGS. 3 and 4 provide a left side view and top view, respectively, of the stimulator 10 showing the conformal shape of the folded antenna 60 inside the epoxy portion 30. The antenna has a shape that includes two arcs which arcs are connected together on one end of each arc. It can be seen that the antenna is thereby folded in a manner to provide the longest antenna length and maximum possible separation between the antenna and the metal portion of the housing in order to minimize interference.

Figure 5:
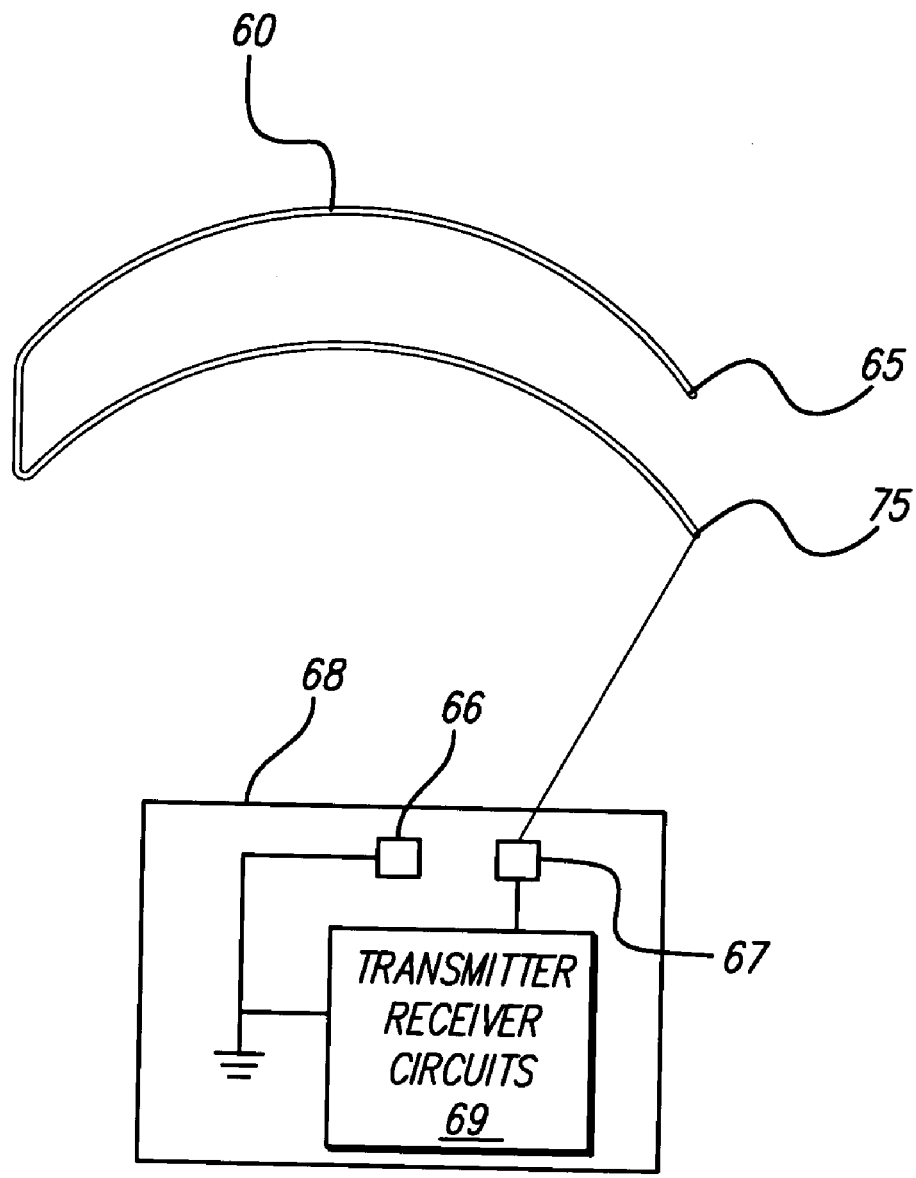
FIG. 5 is a schematic, block diagram of the antenna system of the present invention.

FIG. 5 shows a schematic block diagram of the folded monopole RF antenna system of the present invention. The folded monopole antenna 60 has free end 65 and connection end 75 which, in the embodiment shown, is coupled to metal connection pad 67 on the internal printed circuit board 68. This metal pad 67 is further connected to a receiver/transmitter circuitry 69. The receiver circuit senses, amplifies and processes induced currents captured by the antenna 60 and the transmitter circuit can transmit signals back to a programmer via the same antenna. The receiver and transmitter circuitry can only operate one at time. Software programming may be employed to control a switch which turns one circuit on and the other circuit off during a particular time interval. Both the receiver and transmitter circuits are connected to a common circuit ground. This ground is connected to a second connection pad 66 on the printed circuit board 68, which connection pad 66 is also electrically connected to the metal housing acting as a ground plane. Using the metal housing as a ground plane increases the effective length of the antenna and beneficially shapes the RF radiation pattern of the antenna. In another embodiment, the second metal pad 66 may be alternatively attached on the inside or outside surface of the metal housing, instead of the internal printed circuit board.

The resonant frequency of the antenna, as implanted, depends on the dielectric values of the epoxy and body tissue, as well as the actual length of the conductor wire within the epoxy. The epoxy is used to insulate the antenna from the body tissue and, as such, the epoxy must be biocompatible for long-term implantation. In addition, the epoxy chosen should have a relatively high dielectric constant and exhibit low signal losses. Taking into account the choice of epoxy and the intended placement in the body, a desired resonant frequency of the antenna can be obtained by varying the length of the antenna.

The above-described antenna has been fabricated and its properties have been measured. The antenna used a 78 mm long copper wire of 20 AWG. One end of the antenna was attached to the metal case and the entire antenna was embedded within an epoxy having $\xi_r \approx 3.6$. At a test transmission frequency of 403.5 MHz the antenna's measured input impedance in air was 18-j176. In simulated body fluids the measured input impedance was 18-j11. When pressed against the body, the antenna provided an input impedance of 19-j9 which was comparable to the results obtained in simulated body fluids.

Figure 6:
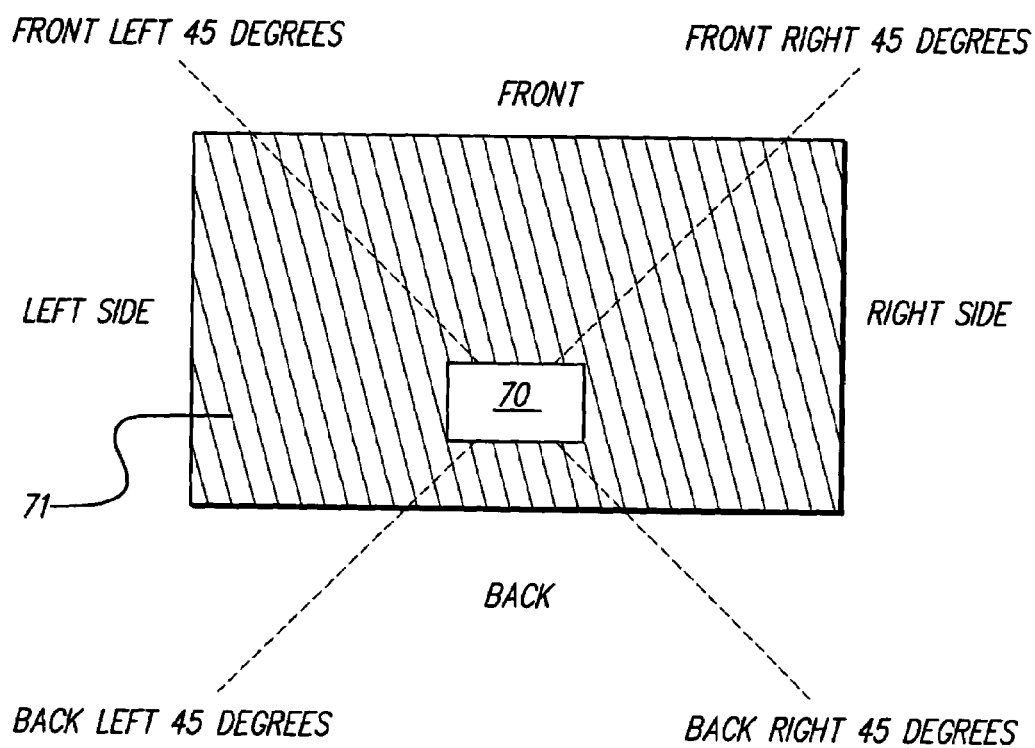
FIG. 6 is a diagram showing the various directional placements of a test receiving antenna relative to a test transmitting antenna which is located in a simulated body.

FIG. 6 shows a diagram of a test set-up for a directional detection test in which a simulated spinal cord stimulator is implanted into the back of a patient. A pair of commercially available Chipcon CC1000 demonstration bread boards operating at a transmission frequency of 433 MHz was used to determine the detection distances of a test folded monopole antenna relative to variable positions of a test transmission antenna. On one bread board, the test, folded monopole antenna was attached to the transmitter, while on the other bread board, a helical (stub) monopole antenna was attached to an external transreceiver. To simulate body tissue, a phantom gel was concocted to simulate the RF transmission attenuation properties of the tissue. The monopole antenna and battery were connected to the test bread board and these were placed inside a polybag which, in turn, was immersed in the gel material simulating body tissue. As seen in the FIG. 6, the test antenna system 70 was located in the simulated body tissue 71 towards the back of the simulated body.

During the test, the transmitter output was set to −15 dBm, the maximum power that would be permitted with an ideal antenna under the MICS regulation. The receiver RSSI (received signal strength indicator) output was used to measure the relative signal strength. An LED indicator was installed to illuminate at just above the detectable level for a 10 kbytes/sec FSK signal and a second LED indicator was set to illuminate at approximately 20 dB above the threshold. This threshold level was used to determine the effective frequency range. The results showed that the resonating characteristics of the antenna placed in the phantom tissue varied little between 403 and 433 MHz.

The measured ranges for detectable transmission distance as a function of position relative to the transmitting antenna (medical device) are shown in Table 1. As shown in FIG. 6 the receiving antenna was placed at various locations relative to the test transmitting antenna 70.

TABLE 1

Detection range test using a folded monopole antenna attached to a transmitter and immersed in a phantom gel. A helical stub monopole was the receiving antenna and the transmitter power was set at −15 dBm.

| Position of External Receiver Relative to the Implantable Stimulator | Detectable Transmission Distance (sensitivity ≈ −90 dBm) |
|---|---|
| Front of simulated body | 91 in |
| Back of simulated body | 269 in |
| Side of simulated body | 194 in |
| Front of simulated body at 45° | 118 in |
| Back of simulated body at 45° | 211 in |

The detectable range was at a minimum at the front of the simulated body, as expected, since the signal travels through the simulated body to reach the receiver. Although the detectable range was at a minimum in front of the simulated body, the effective transmission distance, nevertheless, extended to a respectable 91 inches. A maximum detectable distance was achieved at the back and along the back 45° lines. The antenna was not impedance matched with the front-end RF circuitry of the demonstration board during the test, which may have caused loss of efficiency. The front end RF circuitry, however, can be easily designed to match the 20 ohm resistance of the antenna.

In summary, the improved, folded monopole antenna is a compact structure which does not need a separate tuning component, as this antenna is self-resonating around the frequency range centered around 403.5 MHz. Because the antenna system of the present invention requires no additional circuitry to tune the resonance frequency, scarce battery power is conserved. The antenna system achieves sufficient gain to communicate with an external transmitting antenna up to a distance of 91 inches.

While the invention herein disclosed has been described by means of specific embodiments and applications thereof, numerous modifications and variations could be made thereto by those skilled in the art without departing from the scope of the invention set forth in the claims.

What is claimed is:

1. An RF telemetry antenna system for communications between an external programmer and an implantable medical device, said system comprising:
    an implantable medical device housing including a conductive, metal housing portion defining an internal volume and a dielectric housing portion defining an internal volume;
    a self-resonating, monopole RF antenna contained within the internal volume defined by said dielectric portion of said medical device housing, said monopole antenna having a free end and connection end; and
    an internal transmitter/receiver circuit having a ground reference located within the metal housing portion that is connected to the metal housing portion such that the metal housing portion acts as a ground plane;
    wherein the monopole RF antenna has an elongate form with at least one folded portion and is conformed inside the internal volume defined by the dielectric housing portion, wherein transmissions from the at least one folded portion are receivable outside the dielectric housing portion, and
    wherein the connection end of the antenna is connected to the internal transmitter/receiver circuit.

2. The system of claim 1, wherein the monopole RF antenna is coupled to the transmitter/receiver circuit that is placed on an internal, printed circuit board.

3. The system of claim 1, wherein the dielectric housing portion is a biocompatible epoxy and the metal housing portion is titanium.

4. The system of claim 3, wherein the epoxy has a dielectric constant $\xi_r$ of about 3.6.

5. The system of claim 1, wherein the antenna elongate form is a conductive wire.

6. The system of claim 1, wherein the antenna is made from a conductive material from the group consisting of copper, platinum and gold.

7. The system of claim 6, wherein the antenna is formed from copper wire that is 20 AWG.

8. The system of claim 1, wherein the antenna elongate form is a conductive strip.

9. The system of claim 1, wherein the RF monopole antenna is folded within the dielectric housing portion to provide maximum separation between the folded monopole antenna and the metal housing portion.

10. The system of claim 9, wherein the folded monopole antenna is formed into a shape comprising a first arc and second arc, wherein the first arc is in a first plane and the second arc is in a second plane, which planes are substantially parallel to each other.

11. The system of claim 1, wherein the RF monopole antenna is sized to provide an antenna self-resonance frequency of about 403.5 MHz.

12. The system of claim 1, wherein the dielectric housing portion is a portion of a substantially flat, elliptical cylinder.

13. The system of claim 1, wherein the monopole RF antenna is embedded in the dielectric housing portion.

14. An implantable medical device, comprising:
a housing having a dielectric portion defining an internal volume and a metal portion defining an internal volume;
a transmitter/receiver circuit located within the housing; and
an elongate monopole RF antenna, with a connection end, a free end and at least one fold between the connection end and the free end, operably connected to the transmitter/receiver circuit and positioned entirely within the dielectric portion internal volume such that the free end is closer to the connection end than the at least one fold.

15. An implantable medical device as claimed in claim 14, wherein the dielectric portion of the housing includes a curved region and the antenna includes first and second arcuate portions that extend along the curved region.

16. An implantable medical device as claimed in claim 14, wherein the transmitter/receiver circuit is connected to the metal portion of the housing.

17. An implantable medical device as claimed in claim 16, wherein the transmitter/receiver circuit includes a ground reference and the ground reference is connected to the metal portion of the housing.

18. An implantable medical device as claimed in claim 14, wherein the antenna comprises one of an elongate conductive wire and an elongate conductive strip.

19. An implantable medical device as claimed in claim 14, wherein the housing defines a substantially cylindrical shape having a central axis and the dielectric portion and the metal portion are separated by a plane that is parallel to the central axis.

20. An implantable medical device as claimed in claim 14, further comprising:
a spinal cord stimulation circuit within the housing.

21. An implantable medical device as claimed in claim 14, wherein the elongate monopole RF antenna is embedded in the dielectric portion of the housing.

22. An implantable medical device, comprising:
a housing having a dielectric portion, defining an internal volume and including a curved region, and a metal portion defining an internal volume;
a transmitter/receiver circuit located within the housing; and
an elongate monopole RF antenna, with at least one fold and first and second arcuate portions that extend along the curved region in first and second planes that are substantially parallel to one another, operably connected to the transmitter/receiver circuit and positioned entirely within the dielectric portion internal volume.

23. An implantable medical device, comprising:
a housing having a dielectric portion defining an internal volume and a metal portion defining an internal volume;
a transmitter/receiver circuit, located within the housing, including a ground reference connected to the metal portion of the housing;
a tissue stimulation circuit located within the housing; and
an elongate antenna with at least one folded portion operably connected to the transmitter/receiver circuit and positioned within the dielectric portion such that transmissions from the at least one folded portion are receivable outside the dielectric portion.

24. An implantable medical device as claimed in claim 23, wherein the dielectric portion of the housing includes a curved region and the antenna includes first and second arcuate portions that extend along the curved region.

25. An implantable medical device as claimed in claim 23, wherein the antenna comprises a monopole RF antenna.

26. An implantable medical device as claimed in claim 23, wherein the antenna comprises one of an elongate conductive wire and an elongate conductive strip.

27. An implantable medical device as claimed in claim 23, further comprising:
at least one lead connector associated with the dielectric portion and operably connected to the tissue stimulation circuit.

28. An implantable medical device as claimed in claim 23, wherein the antenna is embedded in the dielectric portion of the housing.

\* \* \* \* \*